(12) United States Patent
Chaiken

(10) Patent No.: US 11,559,203 B2
(45) Date of Patent: Jan. 24, 2023

(54) NONINVASIVE IN VIVO MEASUREMENT OF PH IN CEREBROSPINAL FLUID

(71) Applicant: Joseph Chaiken, Fayetteville, NY (US)

(72) Inventor: Joseph Chaiken, Fayetteville, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 404 days.

(21) Appl. No.: 16/778,285

(22) Filed: Jan. 31, 2020

(65) Prior Publication Data
US 2020/0245871 A1 Aug. 6, 2020

Related U.S. Application Data

(60) Provisional application No. 62/800,101, filed on Feb. 1, 2019.

(51) Int. Cl.
*A61B 5/00* (2006.01)
*G01J 3/44* (2006.01)
*A61B 5/145* (2006.01)
*G01N 21/65* (2006.01)

(52) U.S. Cl.
CPC ........ *A61B 5/0075* (2013.01); *A61B 5/14539* (2013.01); *G01J 3/4412* (2013.01); *G01N 21/65* (2013.01); *G01N 2021/656* (2013.01)

(58) Field of Classification Search
CPC .. A61B 5/0075; A61B 5/14539; G01J 3/4412; G01N 21/65; G01N 2021/656
See application file for complete search history.

(56) References Cited

U.S. PATENT DOCUMENTS

| 6,774,992 | B1* | 8/2004 | Garver | D21C 9/1052 |
| | | | | 356/301 |
| 2019/0277766 | A1* | 9/2019 | Matousek | G01N 21/658 |

OTHER PUBLICATIONS

Fillioe, Seth, et al. "In vivo, noncontact, real-time, optical and spectroscopic assessment of the immediate local physiological response to spinal cord injury in a rat model." Optical Biopsy XVI: Toward Real-Time Spectroscopic Imaging and Diagnosis. Vol. 10489. Int'l Soc. for Optics and Photonics (Year: 2018).*

* cited by examiner

*Primary Examiner* — Dominic J Bologna
(74) *Attorney, Agent, or Firm* — David Nocilly

(57) ABSTRACT

A system and method for determining the pH of tissue in vivo. A Raman spectrometer is used to collect Raman spectra from the target tissue. The Raman spectra are baseline subtracted and assessed to determine the concentration of $HPO_4^{-2}$ and $H_2PO_4^{-1}$ for the purposes of calculating the pH. The approach was validate in vitro using PBS solutions of known pH. The approach was confirmed in vivo using rat and swine models by probing the immediate vicinity of a contusive spinal cord injury (SCI) in the first minutes and hours after injury. Using a dynamic analysis and the Henderson-Hasselbalch equation, the average of (N=12) noninvasive Raman-based pH measurements of CSF was 7.073±0.156 and at >95% confidence there is no statistically significant difference between the Raman-based and the physically sampled results.

14 Claims, 23 Drawing Sheets

| | Injury A | Control A | P value | Injury B | Control B | P Value | Injury C | Control C | P Value |
|---|---|---|---|---|---|---|---|---|---|
| Average of pH | 7.10 n=30 | 6.89 n=27 | 0.001 statistically significant | 7.05 n=30 | 6.83 n=27 | 0.064 almost statistically significant | 7.05 n=30 | 7.03 n=24 | 0.82 Not statistically significant |
| Standard deviation of pH | 0.29 | 0.15 | | 0.45 | 0.46 | | 0.42 | 0.21 | |
| Coefficient of variance of pH | 0.04 | 0.02 | | 0.06 | 0.07 | | 0.06 | 0.03 | |

| | Injury | Control | P Value |
|---|---|---|---|
| Average coefficient of variance of pH | 0.05 n=90 | 0.04 n=81 | 0.001 statistically significant |
| Standard deviation of average coefficient of variance of pH | 0.01 | 0.02 | |

FIG. 15

NONINVASIVE IN VIVO MEASUREMENT OF PH IN CEREBROSPINAL FLUID

CROSS-REFERENCE TO RELATED APPLICATIONS

The present application claims priority to U.S. Provisional No. 62/800,101 filed on Feb. 1, 2019.

BACKGROUND OF THE INVENTION

1. Field of the Invention

The present invention to the noninvasive in vivo measurement of pH in tissues and fluids generally and, more specifically, to an approach for non-invasively measuring pH in cerebrospinal fluid using Raman spectra.

2. Description of the Related Art

Inflammation is a general term for a medical condition first described roughly two millennia ago. Roman physicians Celsius and later Galen provided a guide for medical personnel that defines inflammation in an empirical manner and remains essentially correct today. Redness, swelling, heat, pain, and loss of function are empirical criteria used for centuries to assess a situation and choose a course of action. Today, there are instruments to more precisely and quantitatively characterize these qualities and that provide additional information to guide medical personnel in choosing and executing a course of action. Inflammation itself accompanies the entire injury, reaction and healing processes and the more information that can be obtained over the course of a specific instance of inflammation, the greater are the opportunities to be able to understand and influence the overall process with the probability of concomitantly improved medical outcomes. For example, in the specific case of spinal cord injury (SCI), is maybe possible to avoid permanent loss of function and/or the formation of the glial scars.

The mechanisms surrounding injury to the spinal cord itself are often discussed in terms of primary and secondary injury. The primary injury refers to the immediate effect of trauma, which includes forces of compression, contusion, and shear injury to the spinal cord. In the absence of cord transection or frank hemorrhage (both relatively rare in non-penetrating injuries), the spinal cord may appear pathologically normal immediately after trauma. Penetrating injuries (e.g. knife and gunshot injuries) usually produce a complete or partial transection of the spinal cord. An increasingly described phenomenon, however, is a spinal cord injury following a gunshot wound that does not enter the spinal canal. Presumably, the spinal cord injury in these cases results from kinetic energy emitted by the bullet.

A secondary, progressive mechanism of cord injury usually follows, beginning within minutes and evolving over several hours after injury. The processes propagating this phenomenon are complex and incompletely understood. Possible mechanisms include ischemia, hypoxia, inflammation, edema, excitotoxicity, disturbances of ion homeostasis, and apoptosis. The phenomenon of secondary injury is sometimes clinically manifest by neurologic deterioration over the first 8 to 12 hours in patients who initially present with an incomplete cord syndrome. As a result of these secondary processes, spinal cord edema develops within hours of injury, becomes maximal between the third and sixth day after injury, and begins to recede after the ninth day. This is gradually replaced by a central hemorrhagic necrosis.

To seriously consider the injuries, specificity about the kind and extent of injury is available thanks to improvements in enabling technologies over the past ≈30 years. Near infrared light (NIR) sources, specifically lasers, improved spectral filters and gratings and charge coupled device detectors make noninvasive in vivo and ex vivo Raman spectroscopy in the physiological spectral window routine. Experience in performing spectroscopy in turbid media commonly presented by medically interesting samples has spawned new approaches to performing quantitative and qualitative analysis of such systems in general. Accordingly, there is need in the art for an approach for evaluating injuries that takes advantage of modern advances in technology and, more particularly, spectroscopy.

BRIEF SUMMARY OF THE INVENTION

The present invention comprises the noninvasive in vivo measurement of pH in the CSF using only Raman spectra. A single NIR laser is directed onto the tissue and both the elastically scattered light (EE) and the in-elastically scattered light i.e. light of different wavelength (IE) than was initially directed onto the tissue are collected. The pH calculation can be made using only the IE but any turbidity corrections if needed would require the EE too. The initial biological response to spinal cord injury is initiated by intra- and extracellular chemical signals. A comparison of Raman spectra of injured spinal cord obtained minutes after injury to those of uninjured spinal cord was used to obtain chemical information that precedes the biological response. 29 rats were studied, including both Injured and Control using Raman spectra of spinal cords in vivo. Principal Component Analysis (PCA) indicates that >99% of the variation of these spectra across both Injured and Control groups is accounted for with 3 components. The first component does not vary significantly representing structural materials. The second and third components reflect the variation in the chemistry of the cerebrospinal fluid and is used for the in vivo measurement of pH in the CSF. The consequences of this situation will be reflected in the following section.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of experimental SCI and path of light. A, B and C are reproducible locations where the laser light was staged for 5 minutes to collect Raman spectra. Contusion injury occurred at point B;

FIG. 2 is a 101-7 baseline corrected Raman spectra collected at position A on a spinal cord over 334 minutes post first laser exposure and 314 minutes post SCI at position B;

FIG. 3 is an expanded scale of different 101-7 baseline corrected Raman spectra collected at position C on a spinal cord over 300 minutes post first laser exposure and 314 minutes post SCI at position B. Arrows show Raman features due to aqueous phosphate ions $H_2PO_4^{-2}$ and $HPO_4^{-1}$;

FIG. 4 is a graph of Principal Component 1 for average (N=3) Control and Injured cohort's time course accounting for >95% of total variance for time evolution of both control and injured animals and at all positions A, B, and C. This data was from position C;

FIG. 5 is a graph of Principal Component 2 loadings for average (N=3) Control and Injured cohort's time course accounting for ≈3% of total variance for time evolution of both control and injured animals and at all positions A, B, and C. This data was from position C. We note that these loadings represent variation over the time course of Raman features below 1200 cm$^{-1}$ and others and that within those loading there appear to be features that are linearly related;

FIG. 6 is a graph of Principal Component 3 loadings for average (N=3) Control and Injured cohort's time course accounting for <2% of total variance for time evolution of both control and injured animals and at all positions A, B, and C. This data was from position C. All other components are very small and not considered in this paper;

Figure 14A:
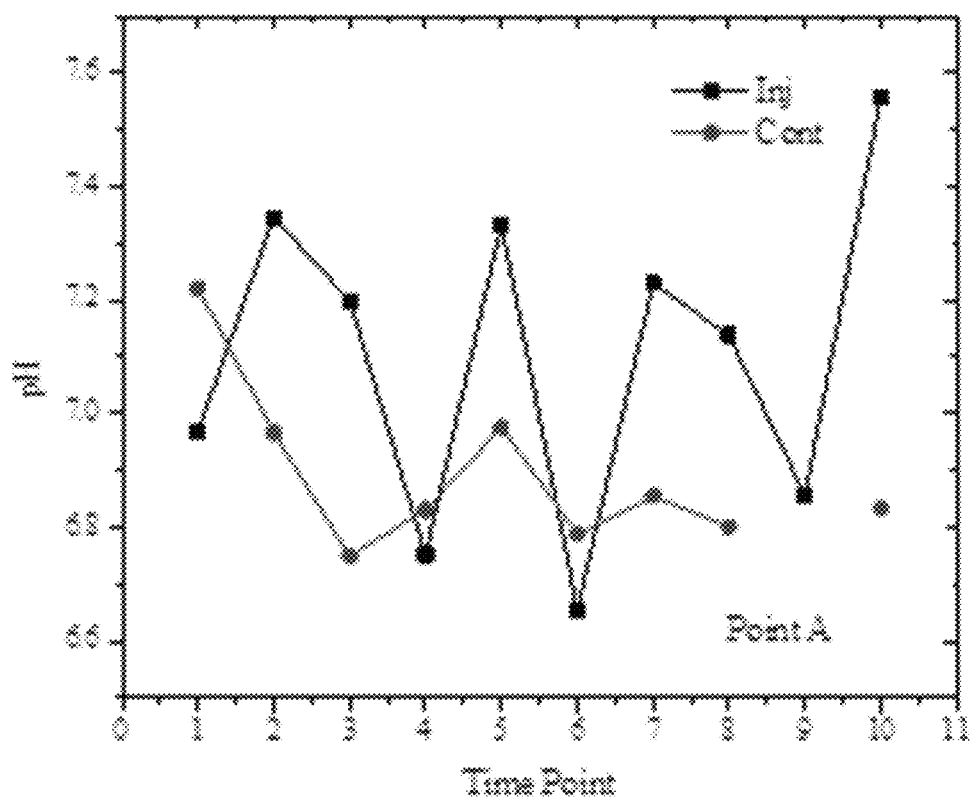
Figure 14B:
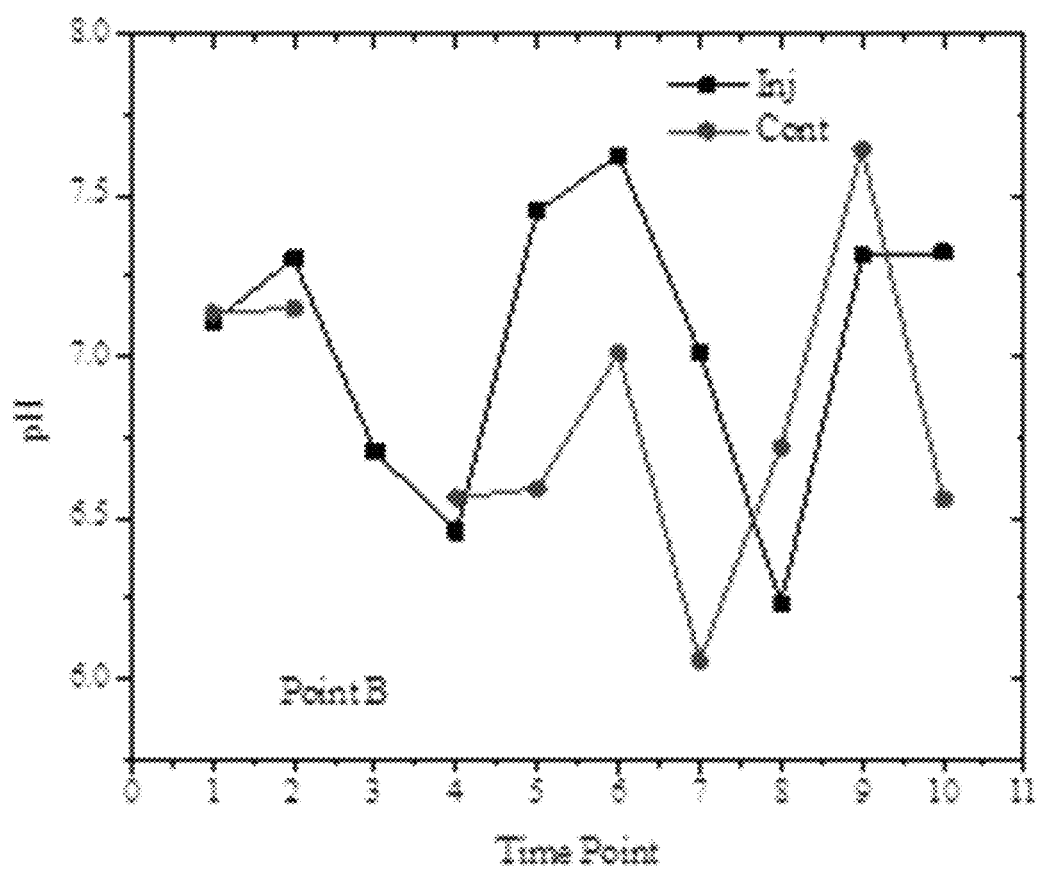
Figure 14C:
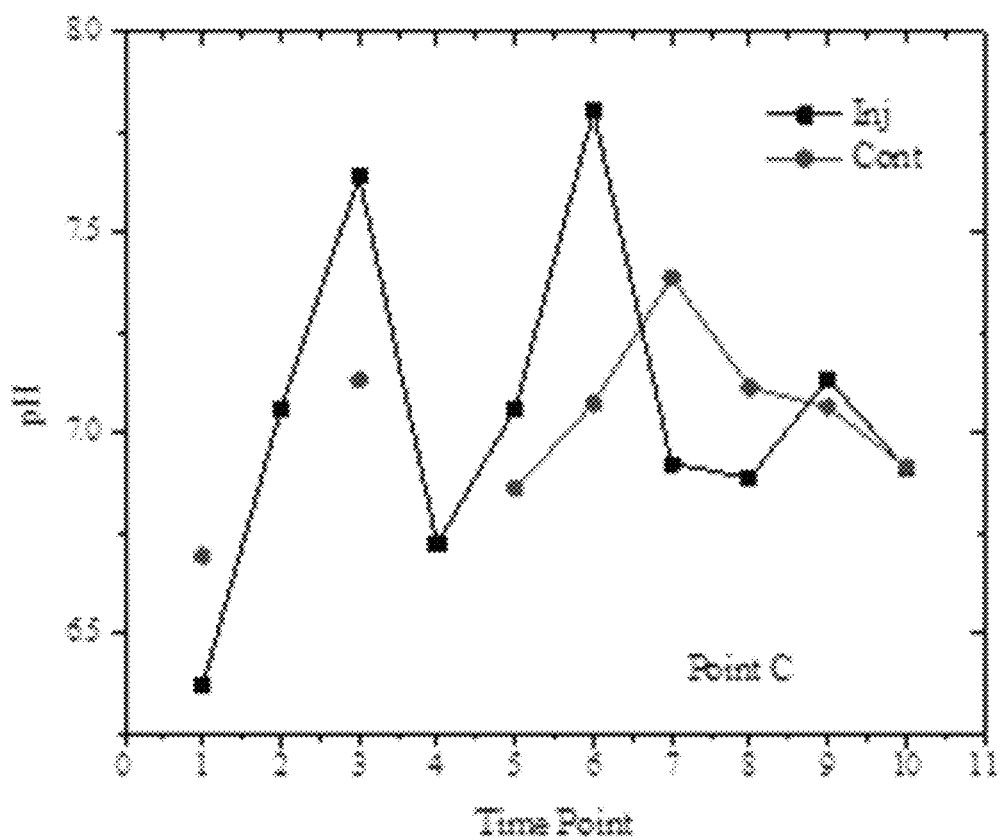
Figure 16:
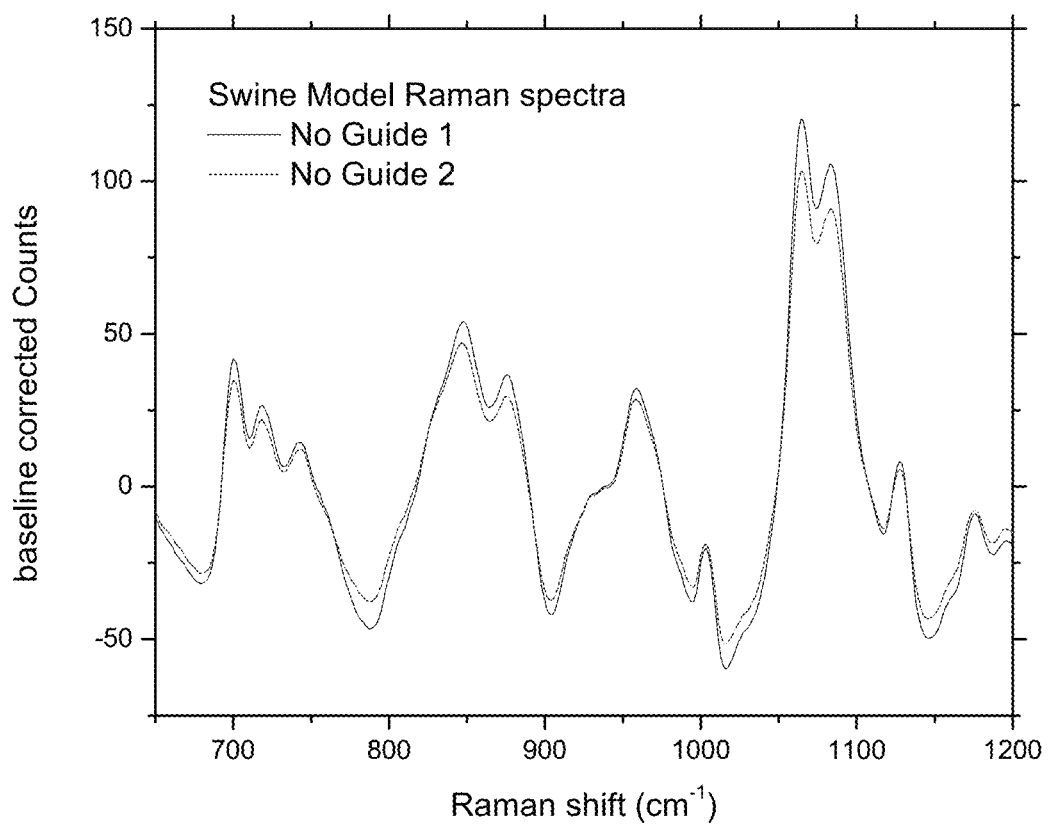
Figure 17:
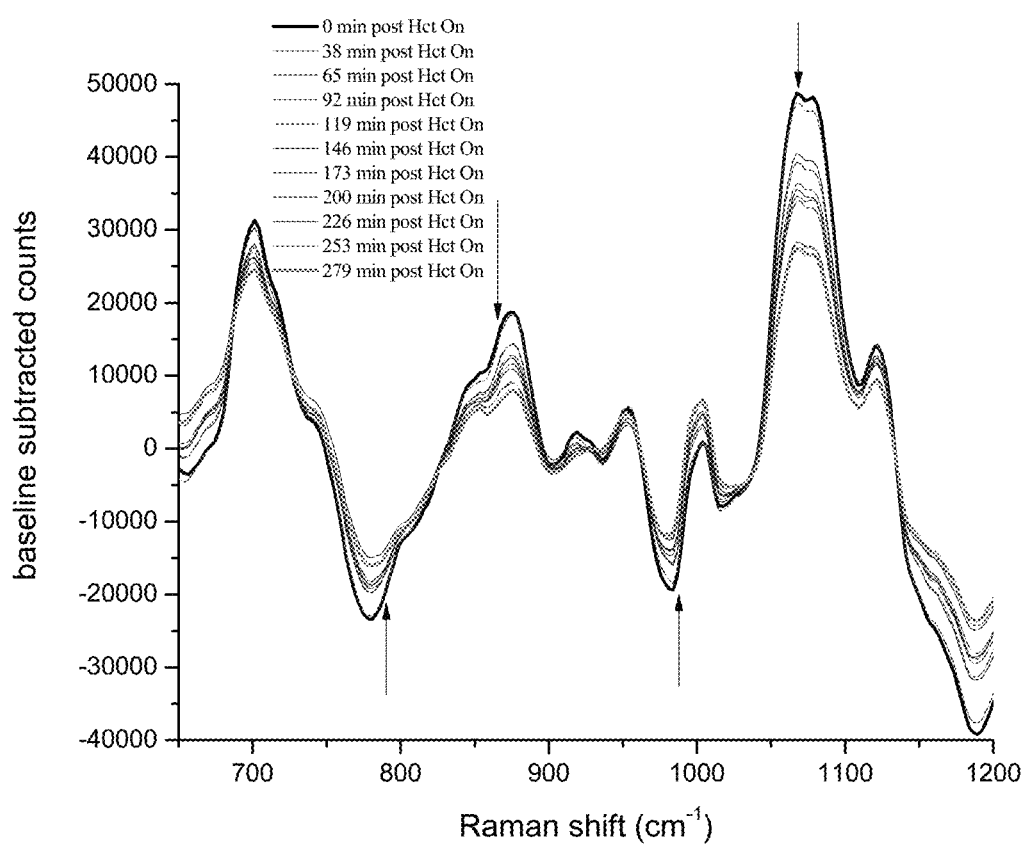
Figure 18:
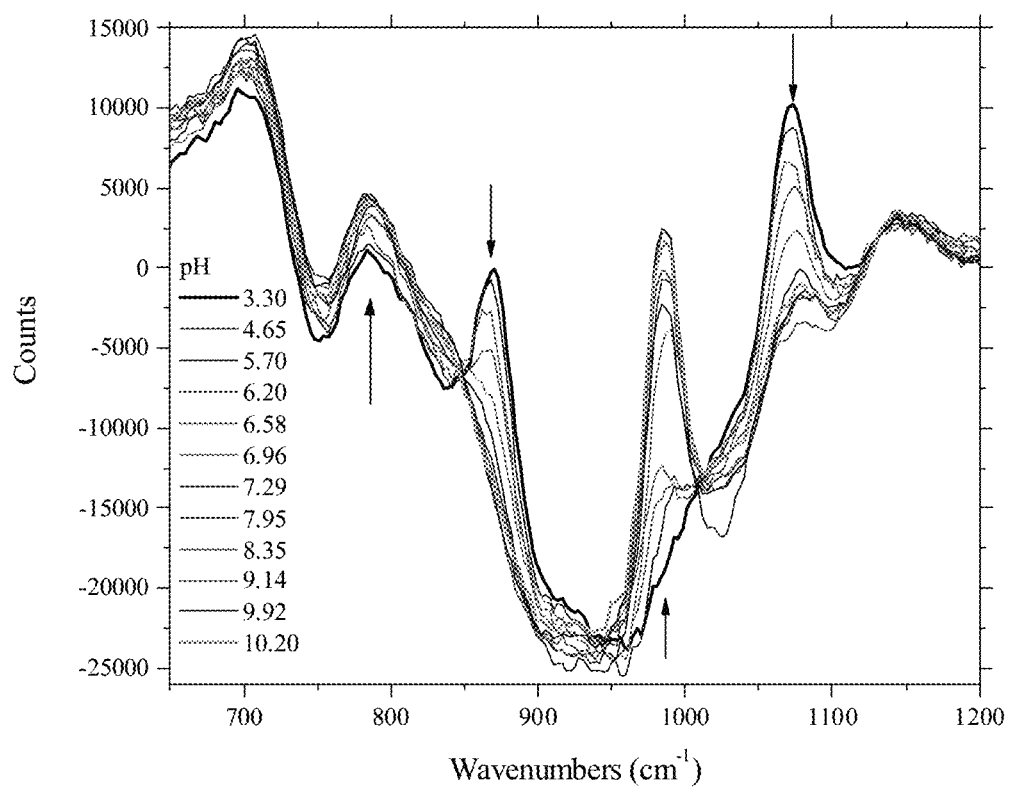
Figure 19A:
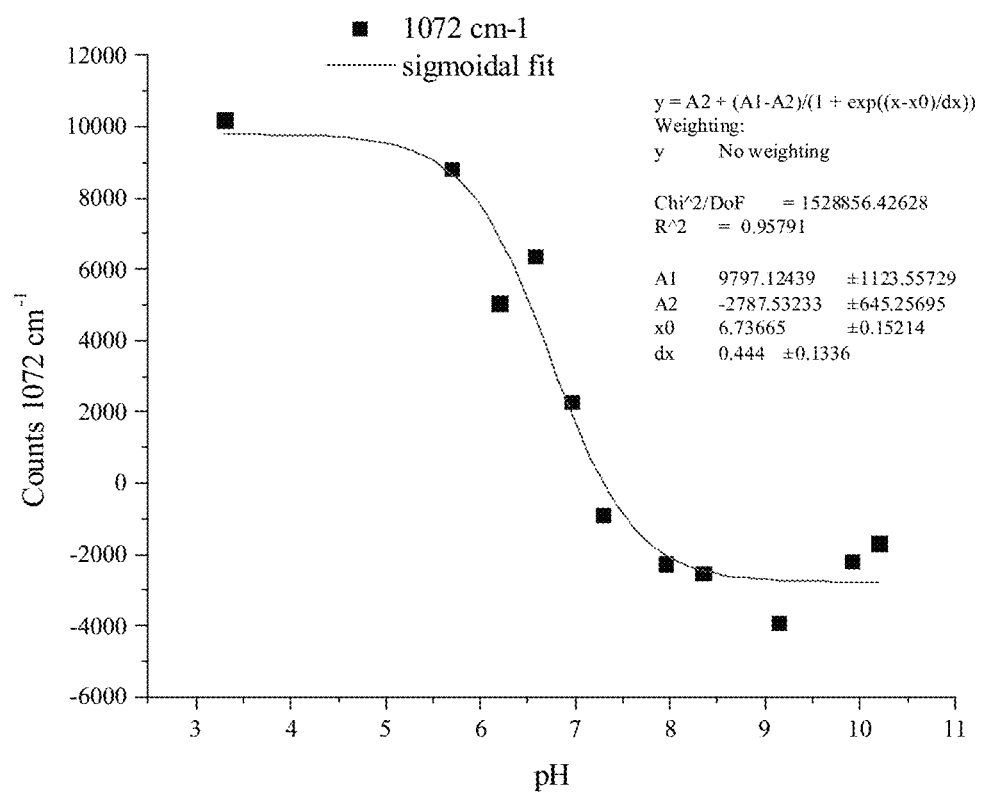
Figure 19B:
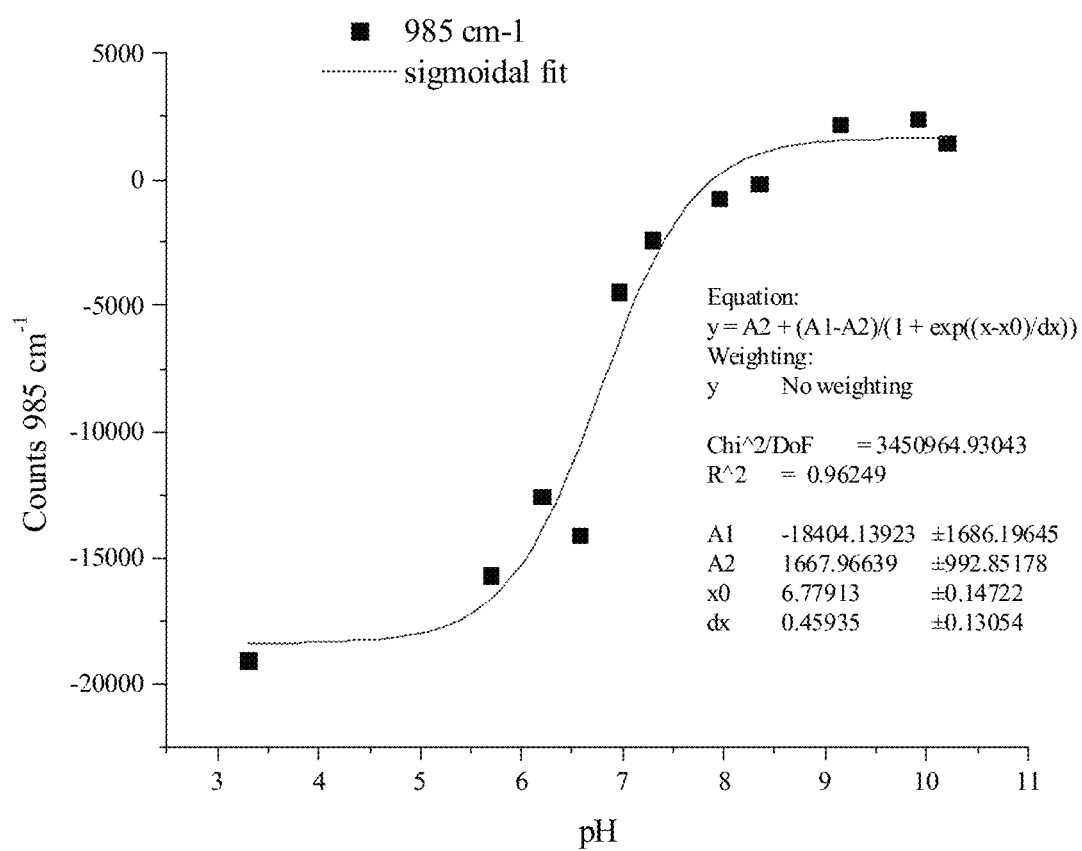
Figure 20:
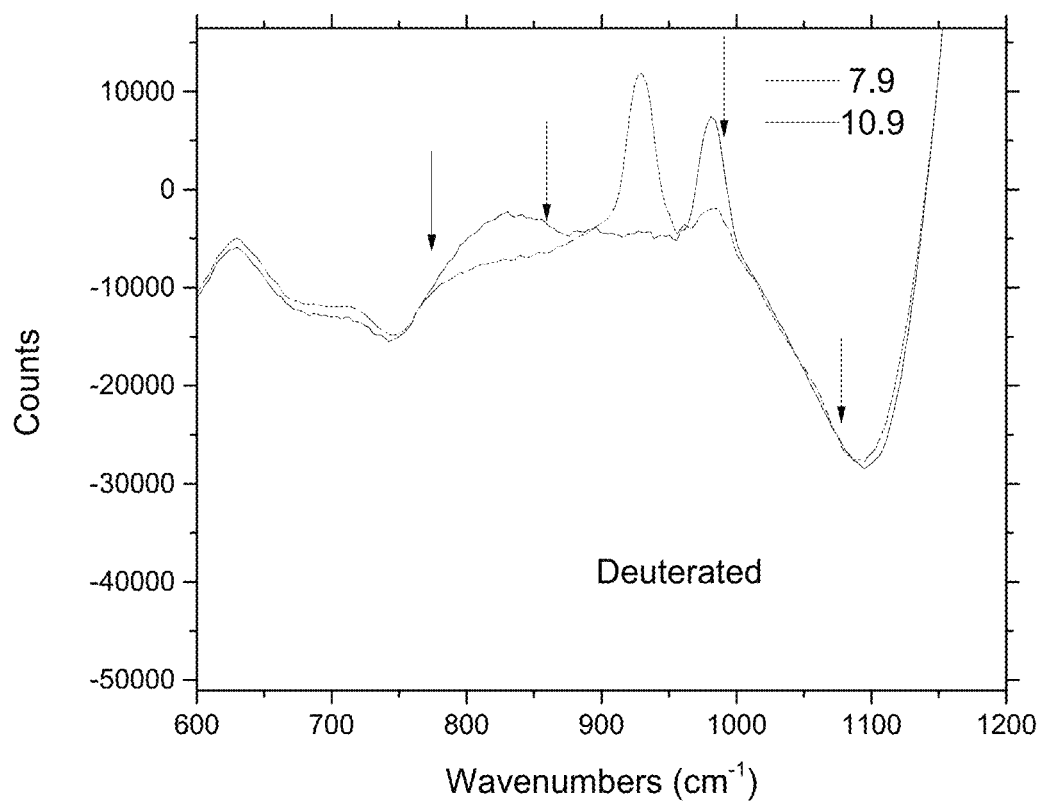

FIG. 14A, FIG. 14B, and FIG. 14C are a series of graphs of comparisons between points and whole classes of injured vs. control;

FIG. 15 is a chart of pH differentiation between locations on an injured cord and between injured vs. control;

FIG. 16 is a graph of the expanded scale of different 101-7 baseline corrected Raman spectra from swine spinal cord;

FIG. 17 is a graph of the expanded scale of different 101-7 baseline corrected Raman spectra collected on a rat spinal cord over 300 minutes post first laser exposure. Arrows above show Raman features due to aqueous phosphate ions $H_2PO_4^{-2}$ and $HPO_4^{-1}$;

FIG. 18 is a graph of the 101-7 baseline corrected Raman spectra collected at same laser power and collection time of aqueous phosphate buffered saline (PBS) which is 10 mM in total phosphate;

FIG. 19A is a first graph of the sigmoidal fit to data taken from 101-7 baseline corrected Raman spectra of PBS as in FIG. 18 for PBS;

FIG. 19B is a second graph of the sigmoidal fit to data taken from 101-7 baseline corrected Raman spectra of PBS as in FIG. 18 for PBS; and FIG. 20 is a graph of the Raman spectra of two different pH solutions of PBS created in $D_2O$ and made more basic with NaOD. The arrows correspond to wavenumbers of interest from FIG. 18. The existence of $PO_4^{-3}$ features affect some Raman features used in the pH calculations more than others causing a shift in the measured $pK_{a2}$ values.

DETAILED DESCRIPTION OF THE INVENTION

Figure 1:
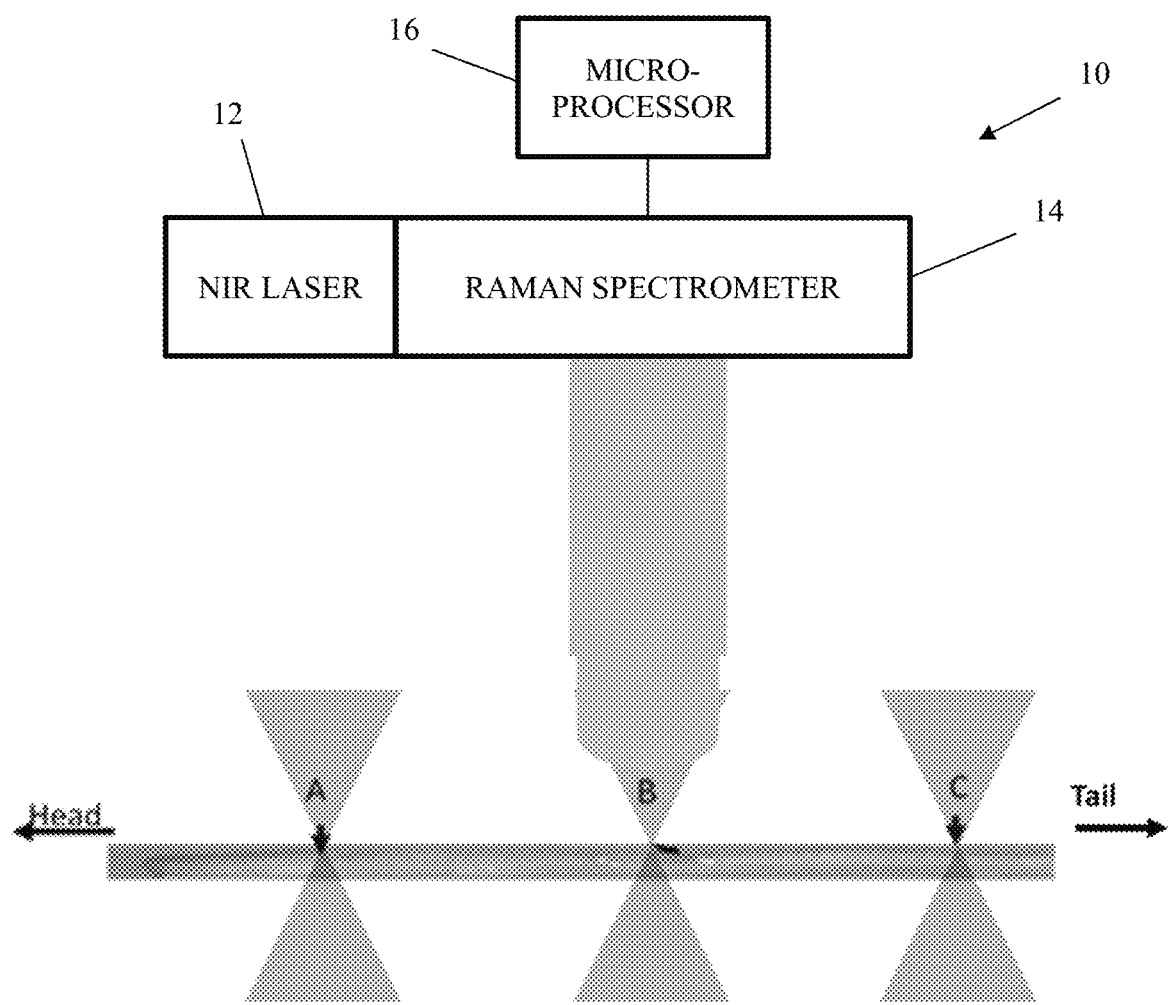

Referring to the figures, the present invention comprises optically probing tissue containing peripheral microcirculation in order to perform quantitative Raman spectroscopy for blood and tissue analysis. As seen in FIG. 1, the present invention 10 includes an illumination source, such as an NIR laser 12 to direct single wavelength energy onto a target whose pH is to be determined, a Raman spectrometer 14 positioned to capture reflected illumination from the site of illumination, and microprocessor 16 configured to interpret the captured Raman spectra and estimate the pH of the target from the Raman spectra.

The present invention thus comprises three primary approaches. First, a single NIR laser is directed onto the tissue of a subject and both the elastically scattered light (EE) and the in-elastically scattered light i.e., light of different wavelength (IE) than was initially directed onto the tissue, are collected. Second, the raw IE will contain broadband fluorescence so it is subjected to a 101-7 or other unbiased baseline subtraction procedure that enables analysis of the part of the raw data that contains Raman transitions. In this procedure, the IE is cropped such that only data corresponding to a specified range of Raman shifts is included and the EE and effects due to spectral filters are excluded. This data comprises a list of raw IE counts at a specified corresponding list of wavenumbers of Raman shifts. These counts data are then subjected to a 101 point adjacent averaging smoothing routine. The smoothing employs equal weights such that the procedure is a convolution of a 101-point simple averaging window across the raw data. This smoothed function is then subtracted from the original raw IE in order to remove as much IE intensity underlying the Raman features while producing a resulting baseline subtracted spectrum that has nearly a zero mean. The 101 subtraction prepares the data for statistical analysis since it comprises the first part of a standard normal variance transform. A 7 point smoothing window is used on the 101 produced difference spectrum to average pixel to pixel noise and shot noise thus comprising the 101-7 process. Third, Raman blood and tissue analysis involves assigning the Raman transitions to specific analytes and using their intensities to calculate pH or other clinically useful quantities, e.g., glucose concentration. This process may be executed with or without the use of the EE, depending on the nature of the sample and the information sought. If the EE is employed the calculation will also employ steps, in addition to those detailed below in this invention, similar to the manner in which the PV[O]H algorithm set forth in U.S. Pat. No. 8,538,499, hereby incorporated by reference, allows a direct calculation of the hematocrit (Hct) and vascular volume (VV) in, for example, perfused tissue. Measurement of some blood-based quantities may require tissue modulation and then the EE would be required for a complete analysis.

In a clinical setting immediately after an SCI, the cord may be accessed surgically for various reasons, e.g., in order to be probed by ultrasound or optically without any need for further physical insult or sampling of any tissues, and then the access could be closed when "noninvasive" NIR probing is complete. A flap could be surgically constructed to allow closing of the surgical field between assessments and easier access later. Depending on circumstances and the kind of information sought, the SCI might be as accessible for optical probing without providing surgical access using fiber optics. This fiber optical probe could be administered like an epidural i.e. inserted between spinal bones near locations chosen based on functional response testing or perhaps MRI results. In the case of a cord exposed for various reasons, once exposed, scanning the laser across the tissue surface and performing the analysis at designated locations would allow for spectral images to be constructed.

Today, there are various robotic assist technologies available in many surgical suites. It would be straight forward to attach a fiber optic coupled Raman probe to one of these robotic appendages to reproducibly scan a section of cord or probe the same location repeatedly.

Since the probing light must penetrate the surface of any tissues in question to produce detectable IE, and the reflective loss at the surface follows the variation in the angle of incidence in accordance with the Fresnel equations, the physical topography and topology of the cord will also be manifest in the spectral response. Using the EE by itself would be optical profilometry and would also allow mapping the surface topography of the cord.

The degree of swelling affects the topology of the cord and that may or may not change over the course of time after injury. The variation of any apparent edema, quantified as apparent Hct, leads to a check for internally consistent imaging. Perhaps most importantly, if Raman spectroscopy is included in the capacity to perform imaging as was originally intended, then the chemistry of the injured cord can also be accessed simultaneously. The construction of images of SCI in a rat model were demonstrated and the results of additional analysis of the Raman spectra obtained in that effort are provided herein.

For clarity, SCI induced by the minimum mechanical insult leading to loss of function was considered. SCI was studied in a rat model involving longitudinal analysis of tissues ex vivo and the cord examined following hemisection SCI in which vascular damage was certain, producing extravascular blood, as well as contusive SCI in which vascular damage was not visually evident using our specific impactor parameters. In the case of hemisection injury, total blood exchange with normal saline preceded tissue harvest and Raman characterization. Both types of injuries produced long-term damage that presented as chemically modified tissues detectable by Raman spectroscopy. In humans, contusive injuries can also result in very significant, permanent loss of function and ultimately a glial scar depending on the severity of the injury. In this study, the focus was on contusive injury.

In the case of mechanical insult, the physically weakest tissues that most effectively absorb the mechanical energy of the insult would be the most vulnerable. The mechanical strengths of the various relevant physical structures of the spinal cord are not known nor their mechanical moduli and the energy impulse delivered by the impactor was not characterized under the experimental conditions. An impactor and probe tip with operational settings expected to produce a mechanical insult that induces moderate injury about 25% of the time was used. This would seem to be a reasonable choice to have enough instances of SCI to produce reasonable statistics while using the smallest cohort of animals. Microscopic examination of the tissues characterized by validated histological staining methods reinforced the conclusions based on the Raman spectra.

Example 1

The present Example relates to a multi-year study involving a cohort of 29. Guided by in vitro Raman spectra of authentic known materials, it is possible to measure pH changes induced by the chemistry of materials released into the CSF by the injury. Consistent with the results of PCA of the entire set of spectra obtained over the course of hours and commencing minutes after impactor induced injury, moderate possible contusive injury is consistent with physical damage and loss of function of the blood brain barrier possibly associated with the choroid plexus The animal protocol used was approved by the Institutional Animal Care and Use Committee (IACUC) of Syracuse University in compliance with National Institute of Health (NIH) guidelines. All surgical procedures were performed in a sterilized surgical suite located in the Laboratory Animal Research (LAR) facility at Syracuse University. Female Sprague Dawley rats, at weight range 250 g to 330 g, were purchased from Charles River laboratories and housed in LAR at least two weeks prior to surgery to acclimate to their environment. Unless specified, all materials were obtained from Thermo Fisher.

The injury model for a rat and all techniques for creating a contusion injury were developed by Rutgers University's W. M. Keck Center for Collaborative Neuroscience division. The contusion injury for all injured animals was produced using the Multicenter Animal Spinal Cord Injury Study (MASCIS) Impactor model III using the standard 3 mm size impaction tip at 12.5 mm above the spinal cord. Previous work with the impactor has stated that the drop distance used for this study can replicate a moderate injury believed to be sufficient for modeling a contusion injury for scanning purposes.

Animals were anesthetized using a procedure standardized in LAR for rat surgery with approval by a certified veterinarian. The surgical steps required to access the spinal cord were described in detail earlier. Using surgical scissors (Fine Science Tools, Foster City, Calif.), a hole is cut into the fat layer beneath the skin and blunt dissection is used to separate the muscle and fat layers; the fat layer is then cut and moved away from the surgical area. In parallel, incisions are made through each of the three muscle layers on either side of the spine. Ultimately, the result is that the dorsal layer of bone for T9 and T10 is removed to expose the spinal cord to a full length of at least 1 cm using Friedman-Pearson Rongeurs. (Fine Science Tools, Foster City, Calif.) The area was cleaned using a saline spray and sterile cotton balls prior to scanning. After completion of the experiment, all animals were euthanized under a standard anesthesia procedure through an overdose of 0.5 ml pentobarbital (Sigma-Aldrich) by intraperitoneal injection.

The spectroscopic measurements employed a modified commercial Raman spectrometer (Lambda Solutions, Waltham, Mass.). The optics and filtering are standard for Lambda Solutions probes but there is an additional Raman notch filter (Semrock, Rochester, N.Y.) placed between the collimating lens and the grating to allow adjustment of the EE and IE for optimum dynamic range in the Hct calculation. These experiments employed a standard Raman normal incidence probe having a focal length of 1 cm and an effective NA of $\approx 0.13$ and the smallest spot size diameter was $\approx 100$ µm. The entire surgical field and in particular the point where light contacts the tissue was kept moist in order to prevent burning during extended exposures. The exterior surface was contacted directly with 80 mW of CW light at 830 nm.

Acquisition of Raman spectra was combined with a scanning protocol in order to account for photobleaching effects, to allow consistent probing of the same locations on the cord at a series of time points, and to allow a long enough signal collection time i.e. 5 minutes to achieve adequate signal to noise in the raw spectra. A "101-7" baseline subtraction algorithm was applied to the raw spectra in order to separate Raman signals from fluorescence before performing either PCA or calculations with Raman signals. The 101-7 procedure makes no assumptions concerning the actual amount of fluorescence or Raman scattering and produces a Raman spectrum that is consistent with standard normal variant (SNV) transformed data i.e. mean of 0 and standard deviation that depends on the data.

PBS solution was made by dissolving 1 PBS table (ICN Biomedicals Inc.) in 100 mL of deionized water. Starting pH was measured at 7.29 using a Vernier LabQuest pH probe. pH was then varied by adding either 1 M hydrochloric acid to lower the pH or 1 M sodium hydroxide to raise it, dropwise into stock solution while stirring. Aliquots were taken from the stock solution and placed into a 1 cm cuvette for analysis after the pH stabilized. The final range of pH in the samples was from 3.30-10.20.

The surgical field is represented in FIG. 1. Considerable care was taken to insure reproducible placement of the laser focus and maintenance of local hydration. The entire experiment was set up on an x-y stage to allow reproducible scanning with respect to a stationary laser. To ensure the injury location on the cord, the stage was modified to include a rail that extended out to the impactor. The probe and focal length were set manually before the animal was moved to the impactor. Three positions (A-C) were determined along the spinal cord based off the insult point of the impactor. Position B was determined as the spot of impact as Position A and C were spaced roughly 1 mm each way (toward the head and toward the hind respectively) on the cord. This allowed for no potential overlap between spots as the spot size i.e. diameter of the laser is roughly 100 μm. This also ensured each spot would be on the cord and not surrounding bone/tissue.

Equal scanning times were achieved for each of the three positions along the spinal cord by placing the stage stationary with light on each point for 5 minutes and scanning from one point to the next for a duration of 5 minutes each, giving a total time of 25 minutes. Once the scanning process was complete, the laser was turned off and the stage returned to the initial position while the animal was monitored to ensure adequate hydration of the injury site as well as continued respiration and anesthesia were maintained throughout the procedure. This procedure was completed a total of 11 times (1 before the impact occurred and 10 following impact) for all animals. On this basis these points are spaced as precisely as possible to 25±3 minutes elapsed time.

Figure 2:
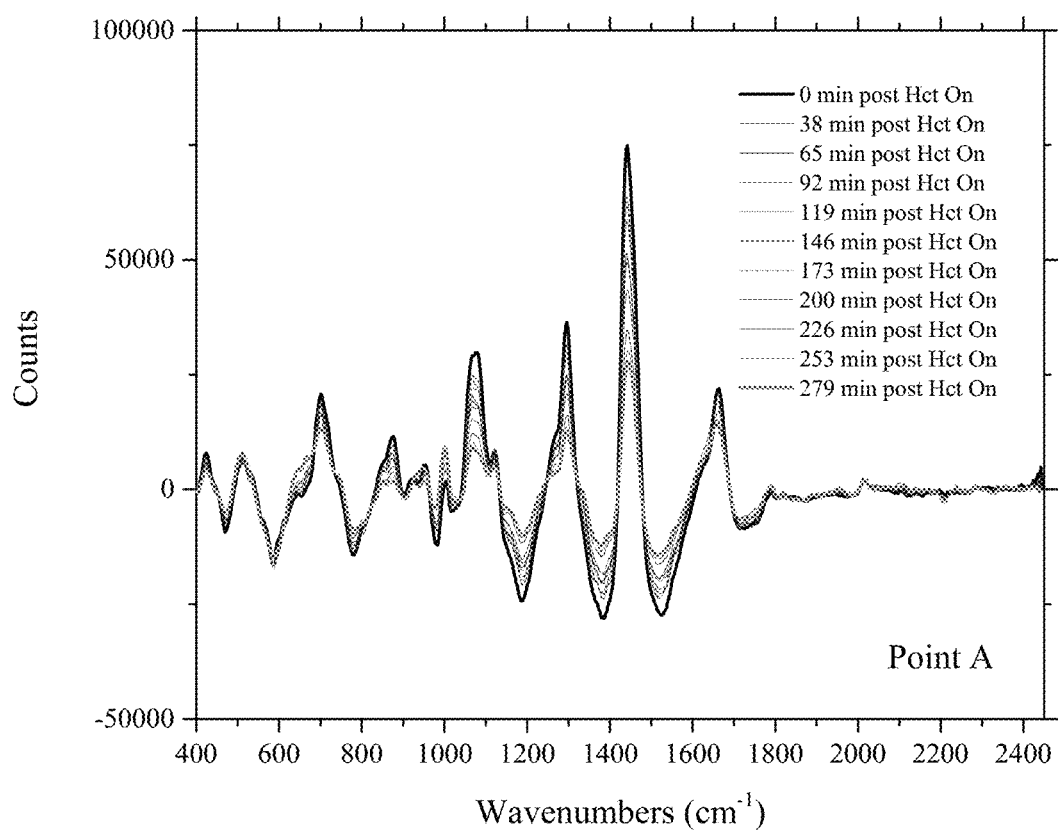

A set of Raman spectra collected as described is shown in FIG. 2 and is representative of the gross features of all spectra at all locations for either injured or control animals. The usual features of $CH_2$ deformation, amide linkages I and III, as well as water at or near 1450 $cm^{-1}$, 1660 $cm^{-1}$, 1300 $cm^{-1}$ and 1670 $cm^{-1}$ respectively are visible and changing over time. Below 1200 $cm^{-1}$ there is similar activity for both injury and control animals that we show in greater detail in FIG. 3. The activity below both decreases and increases at specific wavenumbers as indicated by the arrows whereas above 1200 $cm^{-1}$ Raman activity appears to decrease monotonically.

Figure 4:
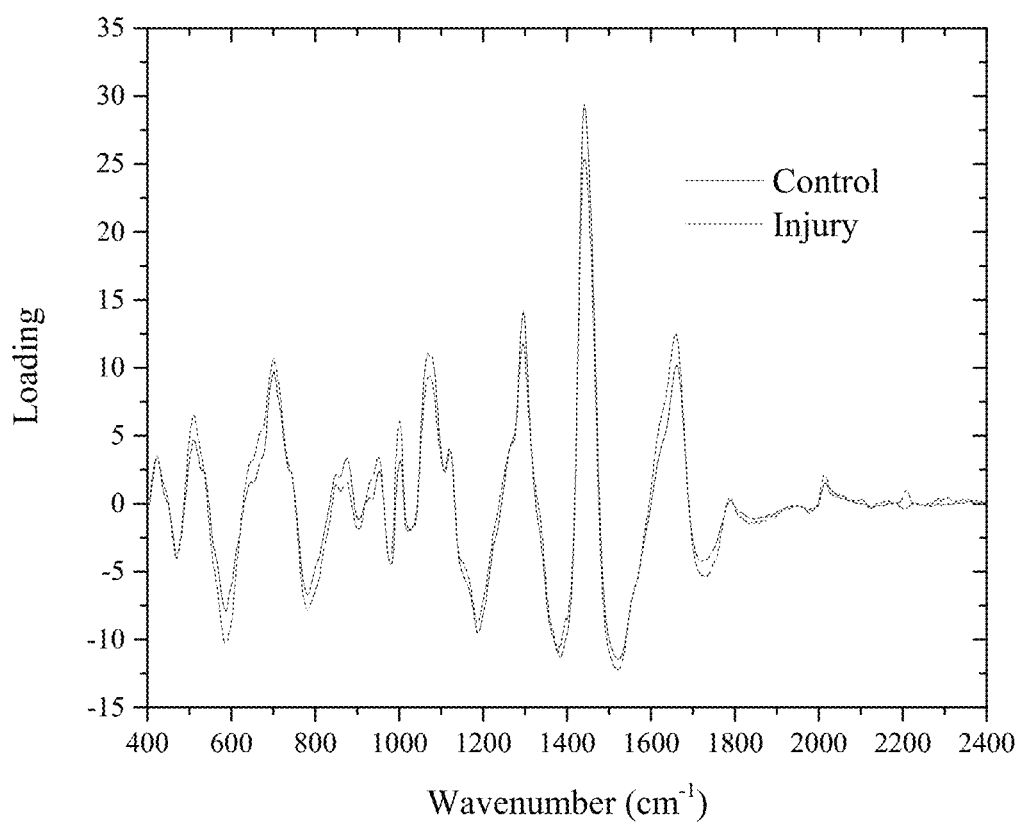
Figure 5:
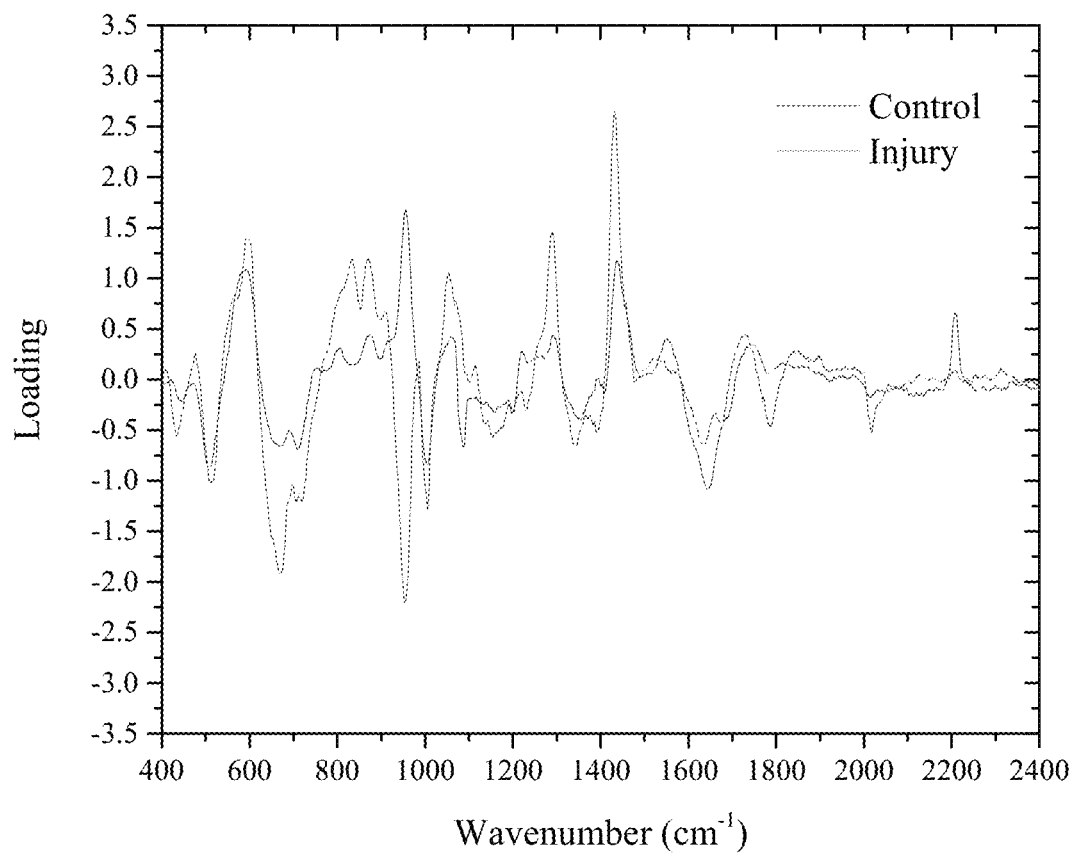
Figure 6:
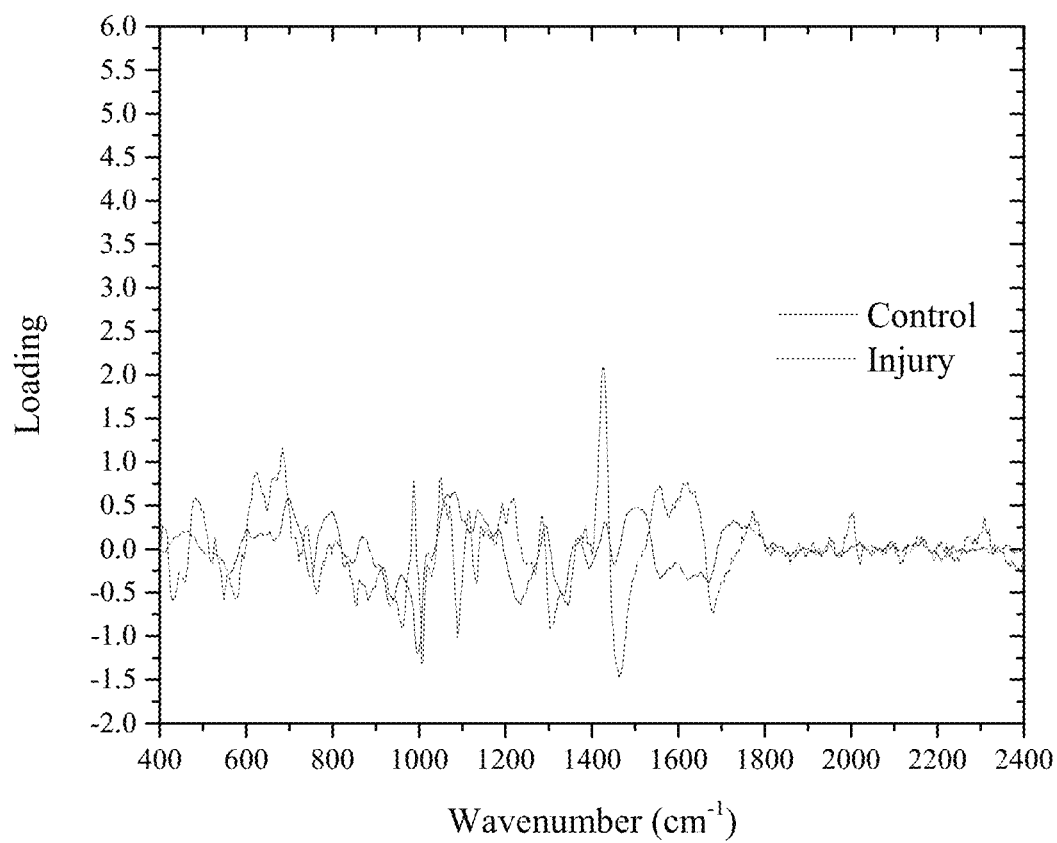

There were 3 control animals and 3 injury model animals and each produced 11 spectra over time that were sufficiently synchronized that they could be averaged across animals to produce an average time sequence for control and injury animals. Each of these sequences was subjected to PCA and the 1$^{st}$ three principal components accounted for greater than 98% of the variance for both control and injury animals. FIGS. 4, 5 and 6 show the loadings for the 1$^{st}$ three components for position C, comparing average injured animal to average control. As is true for all positions, and injured and control cohorts, the first components are very similar.

These loadings represent variation over the time course of Raman features below 1200 $cm^{-1}$ and others and that within those loading there appear to be features that are linearly related.

The Raman spectra and loadings below 1200 $cm^{-1}$ were assessed. Given the probe optics and experimental arrangement, the probed volume corresponds to the outer cord covering, the subarachnoid space which directly below and the fluids therein. We probably penetrate the while matter and possibly even to the grey "butterfly" region therein but there is no evidence that we completely penetrate the cord and obtain signal from tissue below the cord. Given the composition of CSF, which contains much less protein than serum or cells, it was hypothesized that Principal Component 1 is associated with the structural materials in the probed region of the spinal cord. This would include all solid/soft materials within a roughly millimeter of the cord surface. If there were very large numbers of cells e.g. astrocytes present in the inflammatory response to the injury, perhaps they might contribute. But considering the Raman shifts involved and the relatively small contributions of the 2$^{nd}$ and 3$^{rd}$ components to the overall variance, it was suspected that the electrolytes in CSF are mostly involved.

Figure 7:
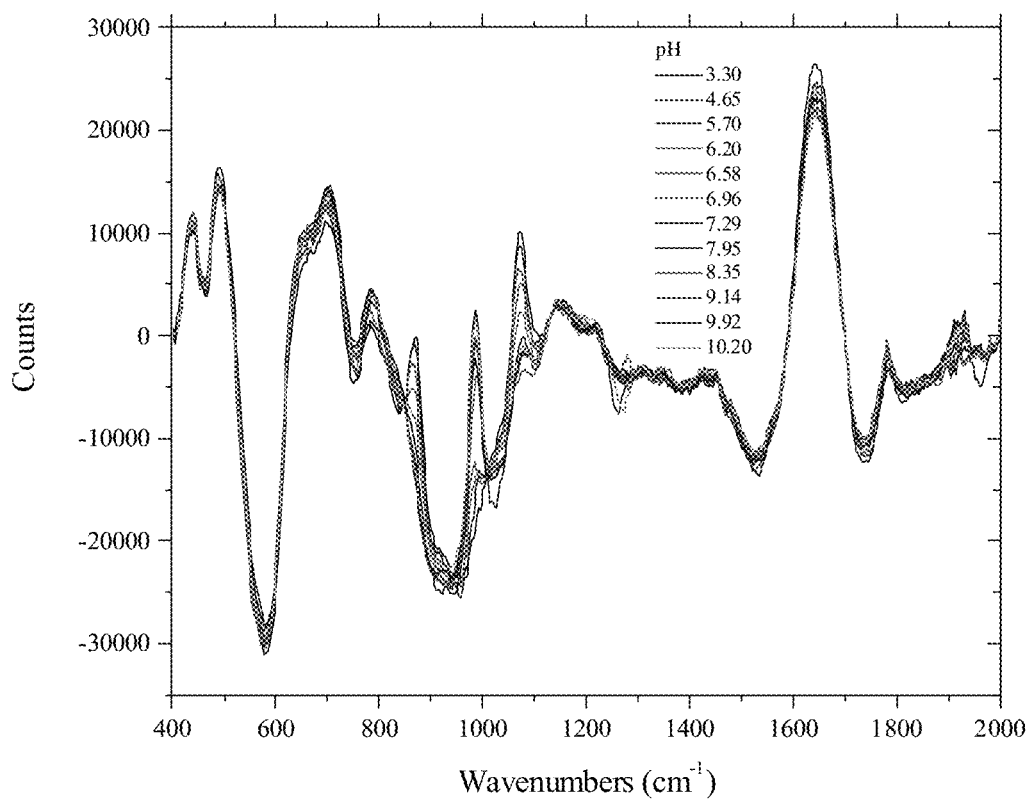
FIG. 7 is a 101-7 baseline corrected Raman spectrum collected at same laser power and collection time of PBS which is 10 mM in total phosphate.

Bicarbonate, which is present in CSF normally in about 20-24 mM concentration, was initially considered and would be expected to vary over time if the oxygenation of any animal changes over time, injured or control. Various attempts to assign observed Raman features in the loadings and spectra themselves to bicarbonate and/or carbonate failed to account for 1) all known features and 2) the relative variation of different Raman features supposedly originating from the same species as will be discussed below. In considering phosphate, even though the normal CSF concentration is at most only about 1.5 mM, all hydration and cleaning of the surgical field was carried out with normal saline with no added phosphate as in PBS. The spectra in FIGS. 7 and 8 were obtained from phosphate buffered saline (PBS) at a range of pH values as indicated with minimum volumes of 1 M HCl and 1 M NaOH being used to adjust the pH.

Figure 3:
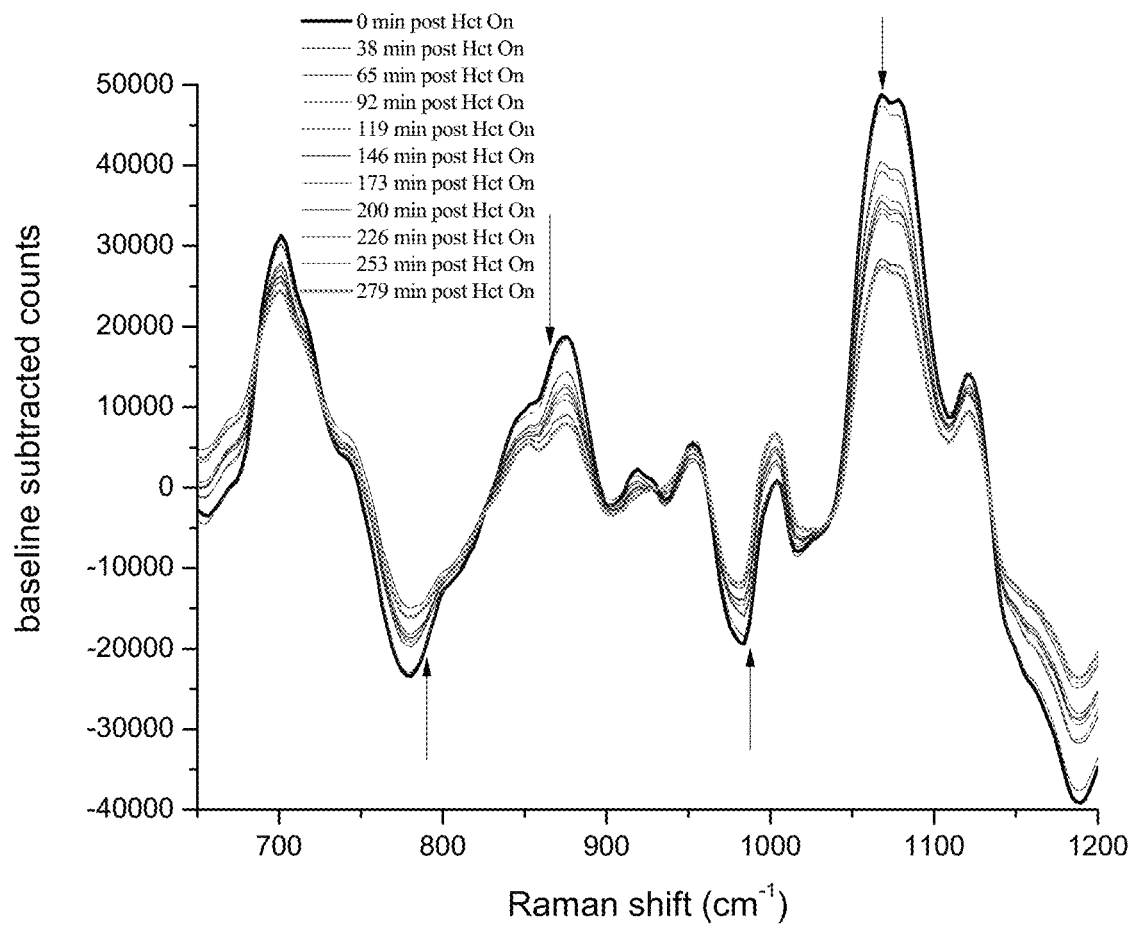
Figure 8:
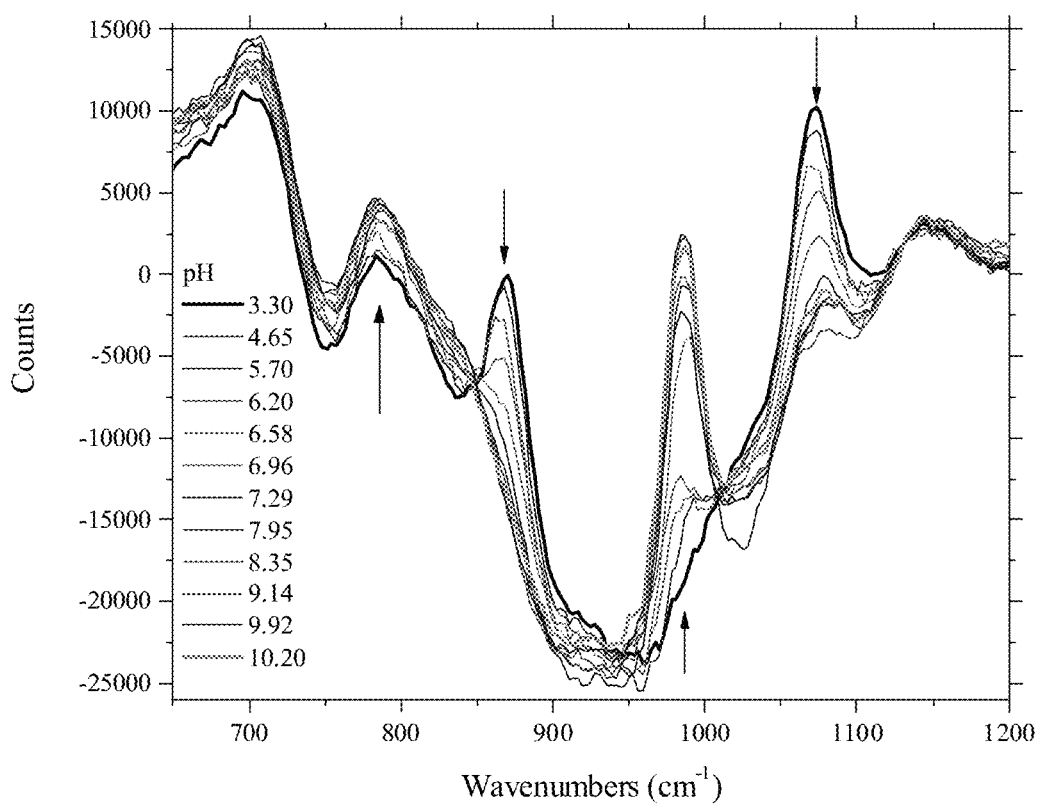
FIG. 8 is a 101-7 baseline corrected Raman spectrum collected at same laser power and collection time of PBS which is 10 mM in total phosphate.
Figure 9:
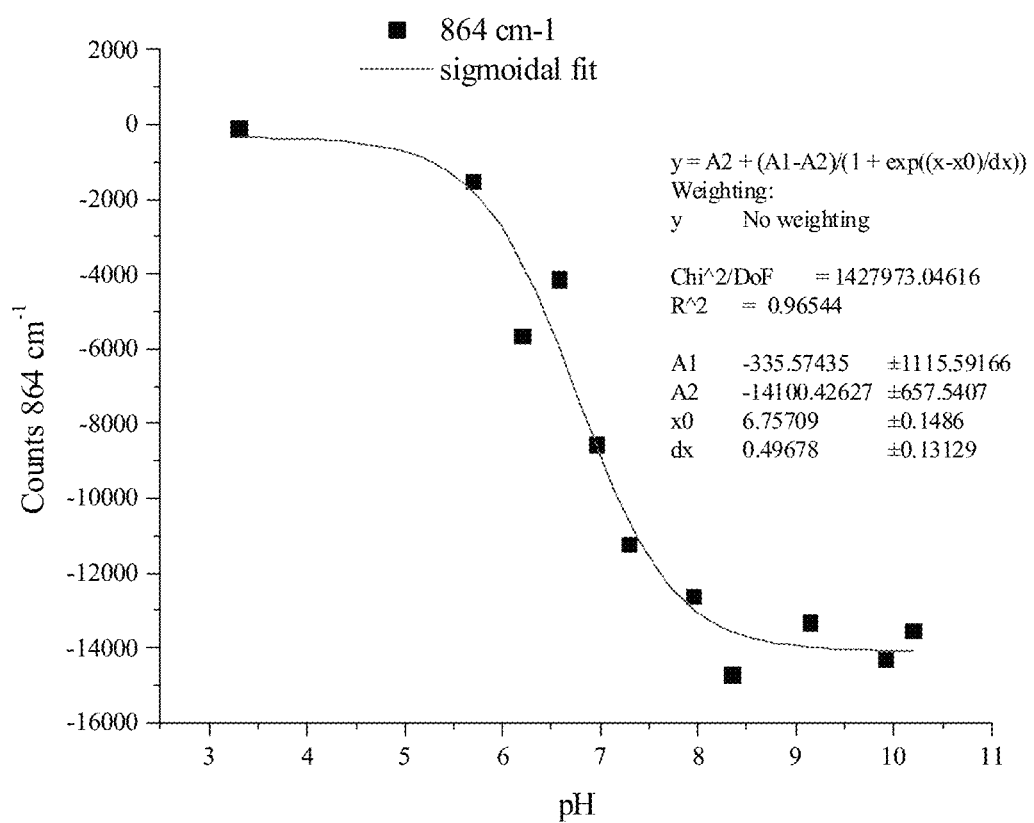
FIG. 9 is a graph of sigmoidal fit to data taken from raw Raman spectra of PBS as in FIGS. 7 and 8 for PBS.
Figure 10:
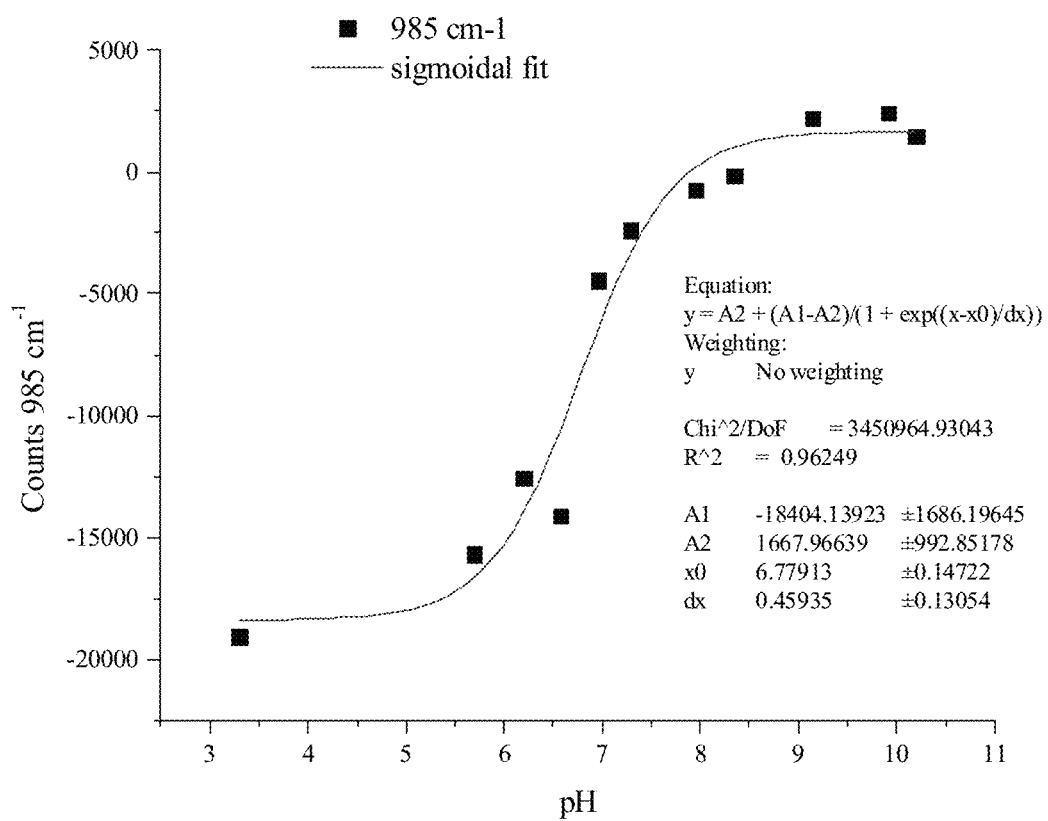
FIG. 10 is a graph of sigmoidal fit to data taken from raw Raman spectra of PBS as in FIGS. 7 and 8 for PBS.
Figure 11:
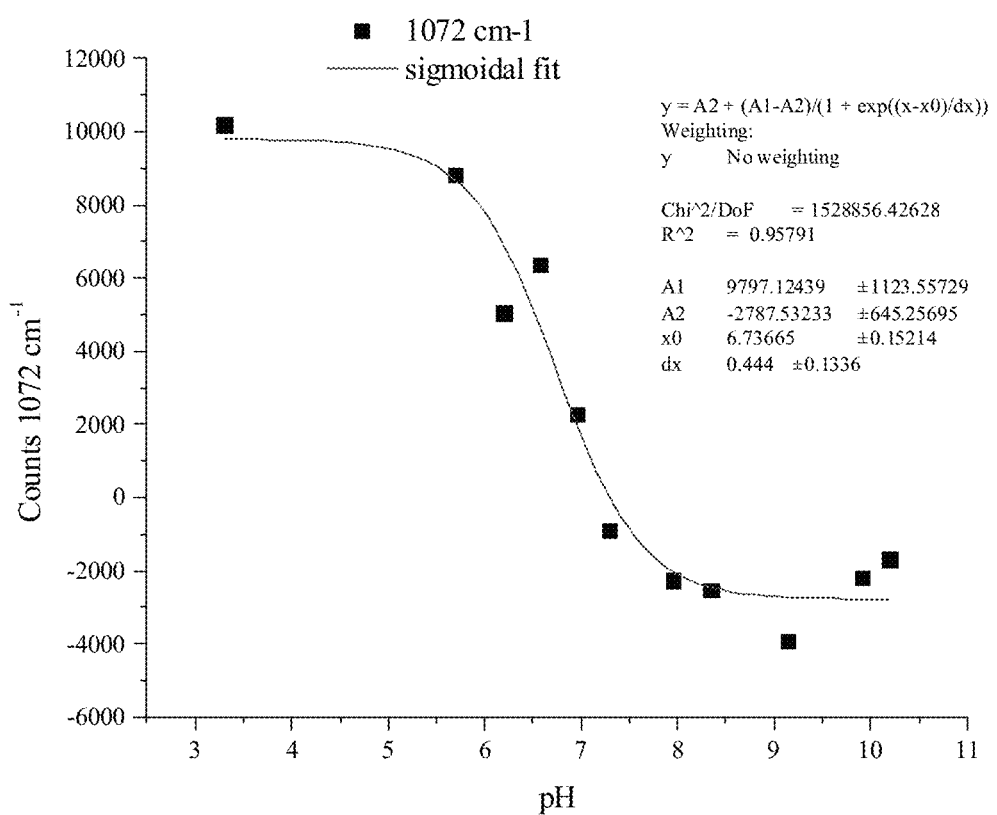
FIG. 11 is a 101-7 baseline corrected Raman spectra collected at same laser power and collection time of PBS which is 10 mM in total phosphate.
Figure 12:
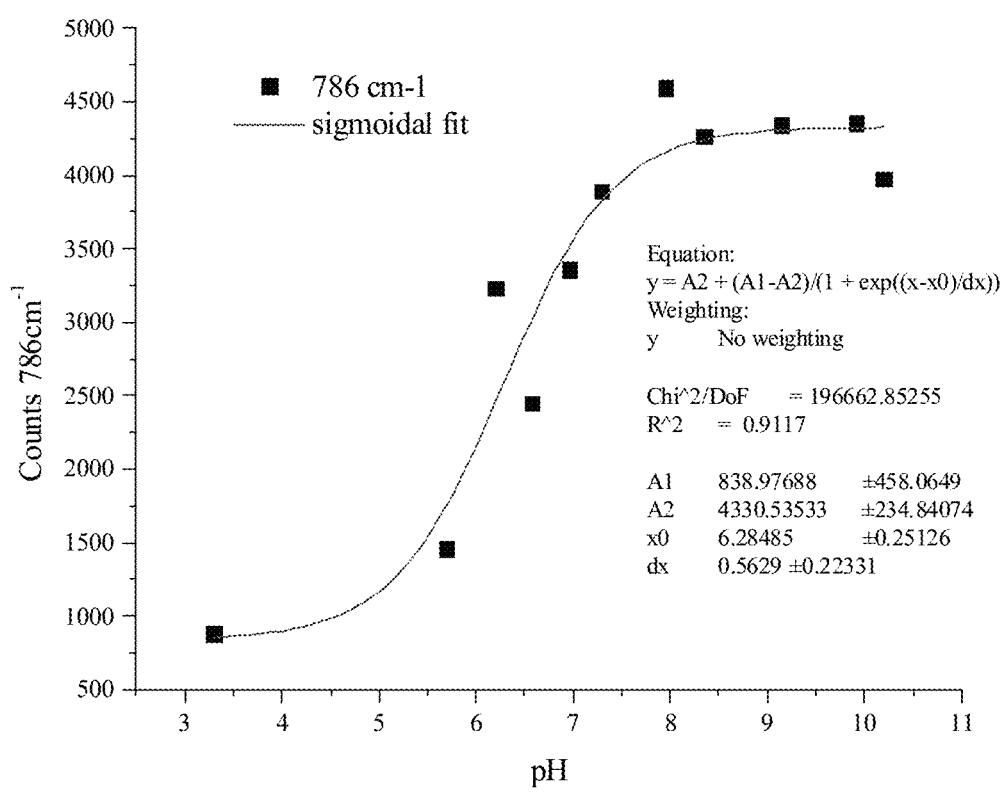
FIG. 12 is a 101-7 baseline corrected Raman spectra collected at same laser power and collection.

PBS has no 1450 $cm^{-1}$, nor 1300 $cm^{-1}$, nor any other indicator of protein. In fact, essentially all features present above 1200 $cm^{-1}$ in the SCI spectra are missing from the PBS spectra except that of water. The arrows in FIG. 3 are in the same wavenumbers as the arrows in FIG. 8 and the exact wavenumbers used were obtained from prior work in the field. Below 1200 $cm^{-1}$ the spectra closely resemble those of the rat cords in vivo. FIG. 8 shows this more clearly and the arrows show Raman features due to aqueous phosphate ions $H_2PO_4^{-2}$ and $HPO_4^{-1}$. Note that essentially: (1) all the features of phosphate are accounted for in the spinal cord spectra over time; and (2) their mutual variation is exactly consistent with the variation of pH as shown in FIGS. 9-12 below.

Similar experiments with bicarbonate as those with phosphate show that it is possible with Raman spectra to account for pH variations in aqueous solution. The data in FIGS. 9-12 result from the titration of phosphate with the exact specific wavenumbers corresponding to the same ones discussed above.

The titration involved is represented by Equation 1 with equilibrium constant $pK_{a2}$.

$$H_2PO_4^{-1} \leftrightarrow H^+ + HPO_4^{-2} \quad pK_{a2}=7.2 \qquad [1]$$

Equation 2 relates the equilibrium constant in terms of concentrations.

$$K_{a2}=[H^+][HPO_4^{-2}]/[H_2PO_4^{-1}])  \quad [2]$$

And using the definitions of pKa and pH we obtain $$pH=pK_{a2}+\log([HPO_4^{-2}]/[H_2PO_4^{-1}]) \quad [3]$$

$$\text{total phosphate}=[HPO_4^{-2}]+[H_2PO_4^{-1}] \quad [4]$$

There are a variety of approaches to relate the data to the pH in the probed volume of the CSF. For example, the data in FIG. 9-12 can be fit to the data to obtain values for $pK_{a2}$ for comparison with the literature. Note that the data in FIGS. 10 and 11 can be used to provide a calibration between counts and mM of each species because the $pK_a$ is well known, the total phosphorus for PBS is known to be 10 mM, and the solution is at equilibrium, whether in the cuvette or in the spinal cord. Within limits, an absolute calibration of counts/mM analyte based on comparing standard spectra to the cuvette and spinal cord is possible, despite turbidity/optical excitation/detection issues, because the optical arrangement is designed to keep us in the single scattering limit. Although, at worst, they should be proportional, i.e., the actual raw counts measured in a cuvette or the spinal cord for a given total inorganic phosphate concentration and pH and might possibly be very similar. Nevertheless, caution was taken in this essentially empirical calibration. Because the present invention involves calibrating between observed counts and actual concentration, i.e., mM, the differences in Raman cross sections for $[HPO_4^{-2}]$ and $[H_2PO_4^{-1}]$ are included implicitly in the resulting calibration parameters.

Successive spinal cord spectra may be different i.e. Controls or Injured because: (1) even at healthy homeostasis materials are flowing into and out of the probed volume; and/or (2) the pH of the liquid in the probed volume is changing. Furthermore, if the liquid in the probed volume is considered to be in chemical equilibrium on a spatial scale of 100 µm and time scale of 5 minutes, then the changes in certain Raman features, i.e., $[HPO_4^{-2}]$ and $[H_2PO_4^{-1}]$ are correlated by the stoichiometry indicated in Equation 1 and the equilibrium constant in Equation 2. These constraints allow use of the absolute value of the successive differences in raw counts for the different features in successive spinal cord spectra to calculate the pH via Equation 3 and the signed differences to calculate any possible change in total phosphate. Using successive differences in this manner removes the necessity of making assumptions as to the appearance of the cord spectra if there was no phosphate present i.e. to assign the raw counts corresponding to 0 mM $[HPO_4^{-2}]$ and $[H_2PO_4^{-1}]$ at the relevant wavenumber Raman shifts.

Figure 13:
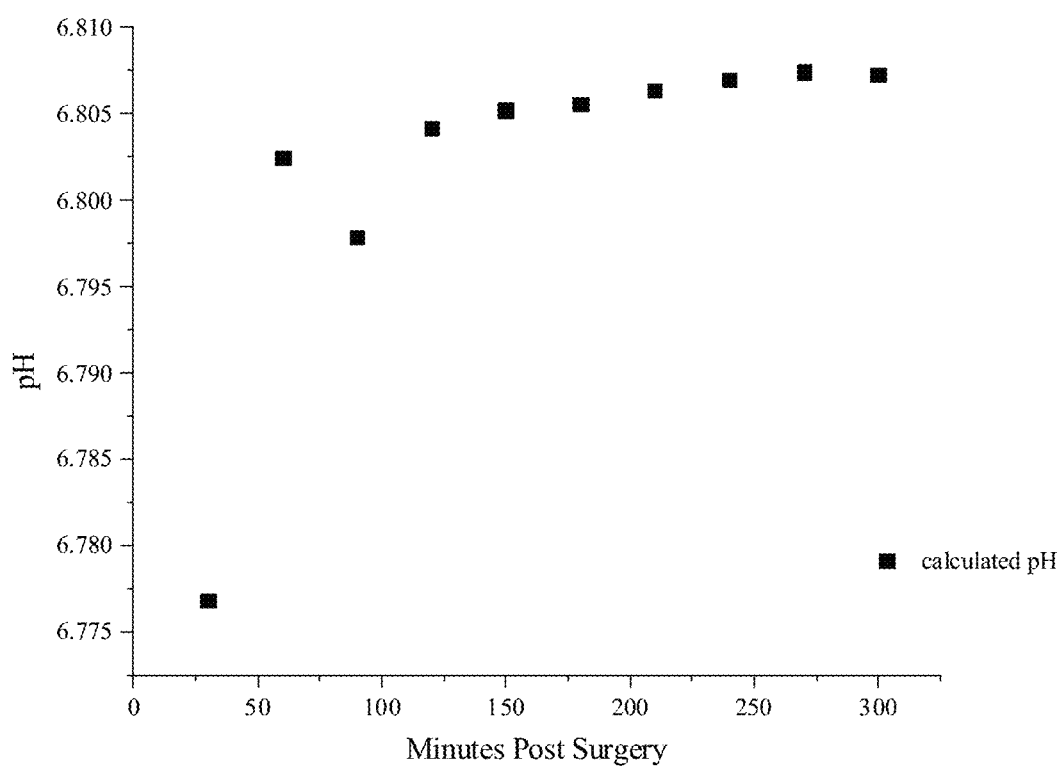
FIG. 13 is a graph of the time course of the raw counts for position B for an injured animal experiment results in the slow drift of pH over the course of time.

These differences can be used in [3] along with the calculated $pK_{a2}$ to calculate the pH of the CSF as shown in FIG. 13. Using the time course of the raw counts for position B for an injured animal experiment results in the pH time course shown in FIG. 13. In general, we note that the time course of the raw counts for the different Raman features reflect a slow monotonic drift of pH upward after an early discontinuity immediately following the injury at position B but only for injured animals. The same general behavior is seen at position C only for injured animals although delayed by about 1-2 hours and for position A, there is no such discontinuity for any animal, injured or Control.

The assignment of the features at 786, 864, 985 and 1072 $cm^{-1}$ in the in vivo spinal cord Raman spectra to inorganic phosphate is unequivocal. Other than amide-based Raman features, $CH_2$ deformation, and possibly certain Raman features that have been assigned to glucose, this assignment is arguably the most certain of any reported to date involving actual in vivo spectra. We suspect this is true because CSF has very little protein and other molecular materials compared to any other bodily fluid, and that limits the amount of spectral overlap that is possible.

The exact wavenumbers correspond to previously published reports. The quantitative relationship between the relative variation of these features over time is identical to that obtained from the authentic materials. In fact, given that normal homeostatic pH of CSF is about 7.3, the variation of all the raw Raman signals are consistent with how the authentic materials would change at about pH 7.3. There are 4 combinations of the apparent inorganic phosphate features that could be used in [3] to calculate pH and all result in the same pH. The pH values calculated from the Raman spectra are consistent with what should be expected based on FIGS. 9-12, i.e., roughly linear drift in the correct, i.e. internally consistent directions.

The possibility that at least some of these features were due to bicarbonate and conjugate acids and bases of such was considered. The assignment was rejected because the variations were not internally consistent. Unless the total amount of bicarbonate associated carbon changes, it is impossible for both carbonate and bicarbonate to increase simultaneously with any change in the pH near 7.2. No such inconsistency is evident for the phosphate assignment. This is not to suggest that there is no spectral overlap between the phosphate and bicarbonate features, or that the amount of bicarbonate associated carbon does not change, only that the amount of bicarbonate increase/decrease is small compared with the amount of phosphate (weighted, of course, by the relative Raman cross sections for the various species) that is present.

If this assignment is accepted, then the strength of the observed phosphate Raman features was be accounted for since normal CSF is only about 0.6 to 1.5 mM in inorganic phosphate, seemingly relatively low given the known sensitivity of Raman spectroscopy. On the other hand, phosphorus itself is more polarizable than many other atoms and based on the spectra in FIGS. 7 and 8 that correspond to 10 mM inorganic phosphate, and it should be possible to collect reasonably good spectra at 1.5 mM. 100 µM solutions for similar phosphorylated molecules can yield useful Raman information using a drop coating technique.

Inorganic phosphate is actively maintained at a level about half that of blood plasma i.e. ~0.4 mM by the choroid plexus. Furthermore, given the normal concentrations of $Ca^{+2}$ and $Mg^{+2}$ and the $K_{sp}$ of the corresponding phosphate salts, we expect that if the inorganic phosphate concentration were to increase very much above ~1 mM, a precipitate would form spontaneously. Also, if inorganic phosphate as $PO_4^{-3}$ or $HPO_4^{-2}$ were to leak across the blood brain barrier due to injury of the choroid plexus, the resulting simple hydrolysis of water in the CSF would increase the local pH.

It has been noted that upon physical disruption of mitochondria in ischemic stroke or brain trauma, and presumably SCI as well, there will be immediate release of phosphates and calcium and a change in pH inter alia. Both scenarios, either damage to the choroid plexus or disruption of mitochondria during contusive injury would result in increased inorganic phosphate in the CSF, potentially precipitate formation, and an increase in local pH, as observed.

While it seems easy to account for the causes and effects, perhaps the most important observation involves the present invention being the first noninvasive in vivo measurement of pH in a bodily fluid. Much as PV[O]H has led to a new type of image construction, the present invention may eventually be able to provide "pH maps/images" of SCI and perhaps even other tissues. The optical conditions that lead to this capability must be compared to those in effect in other tissues, e.g., blood, as they present the possibility that other analytes e.g. glucose can be similarly measured and imaged. With the present invention, it is thus possible to measure pH in vivo, noninvasively in CSF using only Raman spectra of $HPO_4^{-2}$ and $H_2PO_4^{-1}$. In addition, the present invention has demonstrated that moderate, contusive SCI causes the release of chemicals that interact with the CSF causing a disruption in the control of local pH and possibly precipitate formation.

Example 2

The present invention was further tested using a swine model. Swine presents a better model because of fluid volumes that allow physical sampling of CSF using the fourth cerebral ventricle of two different animals, before and after all spectral measurements on cords were completed. One measurement each for two different animals on physically sampled CSF averaged a pH of 7.001±0.106 (N=2) as per standard laboratory instrumentation. Using a dynamic analysis and the Henderson-Hasselbalch equation, the average of (N=12) noninvasive Raman-based pH measurements of CSF was 7.073±0.156 and at >95% confidence there is no statistically significant difference between the Raman-based and the physically sampled results. This example of the present invention continues from the first example both in terms of validating the Raman based measurement of pH and the implications of those measurements on our understanding of the earliest stages of SCI.

All animal model data was collected according an IACUC approved protocol. The swine model experiments were performed perimortem on animals that had just completed a separate and unrelated IACUC protocol conducted by other researchers involving another unrelated part of the animal. Once the animal was deemed perimortem, a section of the spinal column was accessed surgically to expose the cord in approximately the same position as the rat model experiments i.e. T range. Care was taken to not damage the cord during the surgery and the region was thoroughly washed with saline (not phosphate buffered) in order to remove sufficient blood and debris from a region on the cord surface about 3 inches long to allow probing without burning. The section was misted with saline between runs and there was no visual evidence of tissue damage when the procedure was finished.

These swine experiments employed a BWTek i-Raman Pro HT-785 (Newark, Del.) portable Raman spectrometer with 785 nm CW excitation. Spectra were collected as 5 minute exposures, each comprising three hundred, 1 second CCD frames. A set of phosphate buffered saline (PBS) spectra at various pH values were collected for comparison with previously published[4] data obtained with 830 nm excitation. Note that all the rat model data was obtained using 830 nm excitation. The handheld probe was secured with a laboratory clamp to an improvised stand allowing manual placement of the laser spot from the standard probe (Raman Probe HT, 100 μm spot size, working distance 0.5 cm, laser power ≈200 mW, 5 minute total exposure with 300 CCD frames).

The locations for Raman probing were chosen to be relatively white regions without visible underlying vasculature. The probe was placed vertically using a spacer, three spectra were obtained each from a different location roughly along the top of the exposed cord. Once three cord spectra were obtained, the procedure of Kaiser and Frühauf was used to sample CSF via the fourth cerebral ventricle. The CSF was removed using a syringe with an aliquot going directly into the Cobas b 221 (Roche) blood gas and electrolyte analyzer and the remainder stored under liquid nitrogen. After the physical sampling of the CSF, another three cord spectra were taken from locations near but not at the same locations as before.

Only a few spectra are shown here because a full set of rat model data and in vitro calibration data was discussed above. As shown in FIG. 16, the spectrum of swine spinal cord and, in FIG. 17, that of rat spinal cord in the region used to calculated pH are similar but not identical. Given that the rat data was obtained with 830 nm excitation and the swine spectra were obtained with 785 nm excitation, and the system spectral resolution for the 785 nm system is a bit better than for the 830 nm system, but they are still quite similar. The Raman counts at the same Raman shifts shown by the arrows in FIG. 17 in the rat spectra were used to calculate pH. The spectra were all baseline subtracted from the raw spectra using the 101-7 procedure. The 101-7 procedure is unbiased and involves subtracting a 101 point adjacent average of the raw spectrum from the raw spectrum and smoothing that difference with another 7 point adjacent average function.

Since the $pK_{a2}$ of the $H_3PO_4$ system is well known to be 7.2 we note that for both of these species the equivalence point i.e. x0 in the sigmoidal fits occur at lower pH i.e. This discrepancy can be traced to two possible issues. As shown earlier the calibration between Raman counts and e.g. mM $HPO_4^{-2}$ or $H_2PO_4^{-2}$ was obtained by comparison with spectra of the same species at known concentration. Examination of the Henderson-Hasselbalch equation [2] shows that a 10% relative variance in either of these calibrations could lead to the observed discrepancy with the known $pK_{a2}$.

Another distinct possibility involves either feature overlapping with $PO_4^{-3}$ since it will increase in intensity while the others decrease with increasing pH. This possibility is illustrated by the spectra of shown in FIG. 20. In this case, PBS was made entirely using $D_2O$ and NaOD for pH adjustment. In this case there are no protons available and no features are downshifted into the region of interest. In this case there are clear interfering features that can only be due to $PO_4^{-3}$ and these will affect the raw Raman measured concentrations, shifting the ratio in the Henderson-Hasselbalch equation and thereby the calculated pH values. Based on the average discrepancy between the measured $pK_{a2}$ values and the known values, 0.44 was added to all pH values to bring them into mutual agreement. The exact same situation is observed with either the 830 nm or the 785 nm excitation instruments.

FIG. 17 shows that the relevant Raman features drift over time, suggesting two ways of processing these data, as explained earlier. Using the static approach, the average of (N=12) noninvasive Raman-based pH measurements of CSF in the subarachnoid space of the spinal cord, involving 2 swine, six measurements each, all approximately 12 cm caudal to the fourth ventricle, over a period of 60 minutes beginning immediately perimortem, gave a pH of 7.168±0.017. After applying the correction described above, the difference between the average pH measurements of the CSF for physically sampled vs. static Raman based measurements in swine perimortem i.e. 0.167 was statistically significant (p<0.001) although not large. The dynamic method produced 7.073±0.156 and at >95% confidence there is no statistically significant difference between the Raman-based and the physically sampled results. This shown in Table 1:

TABLE 1

Results from pig model comparison with laboratory instrument/physically sampled CSF (Cobas b 221).

|  | Calculated pH Before Removal | Calculated pH After removal | Average Calculated pH with offset (0.44) | Cobas b 221 pH | Difference Ave-Cobas |
|---|---|---|---|---|---|
| Pig 1 | 6.55 | 6.65 | 7.04(N = 6) | 6.93 | +0.11 |
| Pig 2 | 6.60 | 6.66 | 7.07(N = 6) | 7.07 | +0.00 |

With the proper calibration in place Table 2 summarizes the measurements made on rat cords previously described.

Position B is the position where SCI occurred, position A is approximately 1 mm rostral, and position C approximately 1 mm caudal to position B. Note that normal CSF pH is closer to 7.3 and all values obtained here by either physical sampling or Raman spectroscopy are lower by about 0.3. Since the animals were all studied perimortem we would expect the lower pH values because respiration had ceased and there would be $CO_2$ build-up.

TABLE 2

Collected pH results from previous rat model study.

| | Injury A | Control A | P value | Injury B | Control B | P Value | Injury C | Control C | P Value |
|---|---|---|---|---|---|---|---|---|---|
| Average pH | 7.10 n = 30 | 6.89 n = 27 | 0.001 Very statistically significant | 7.05 n = 30 | 6.83 n = 27 | 0.064 Not quite statistically significant | 7.05 n = 30 | 7.03 n = 24 | 0.82 Not statistically significant |
| Standard deviation of pH | 0.29 | 0.15 | | 0.45 | 0.46 | | 0.42 | 0.21 | |
| Coefficient of variance of pH | 0.04 | 0.02 | | 0.06 | 0.07 | | 0.06 | 0.03 | |

| | Injury | Control | P Value |
|---|---|---|---|
| Average coefficient of variation of pH | 0.05 n = 90 | 0.04 n = 81 | <0.0001 |
| Standard deviation of average coefficient of variance of pH | 0.01 | 0.02 | |

In conclusion, there is a statistically significant difference between the pH of CSF for injured rats compared to Control Group. The pH is slightly higher for injured and the difference is larger rostral to the injury site and not statistically different caudal. The coefficient of variation of the pH for all measurements on the Injured Group is greater than that for the Control Group. The pH values are all less than normal, i.e., 7.3, but we note that the animals were under anesthesia and although their color and disposition was pink and stable, we could not validate that they were properly oxygenated.

The pure Raman approach to noninvasive in vivo pH measurement of CSF has been successfully validated against conventional measurements i.e. using physical sampling and conventional laboratory analysis instrumentation. The present invention is the first noninvasive, label free, measurement of pH in a bodily fluid in vivo using only Raman spectra. Either the static or dynamic approaches to data analysis gave pH results that were not very different, i.e. within ±3% (static) or no significant difference (dynamic) from the results obtained from physical sampling and standard laboratory analysis. The dynamic approach may have been better statistically, if less precise, because the raw measurements were more associated with underlying fluids and the static approach could have had some artifact perhaps features associated with structural materials produced a false baseline. Formal studies of accuracy and precision will require more time and animals.

The literature of SCI and neuronal death suggest various possible reasons for lack of pH control of injured neurons including impaired neurotransmitter uptake and/or rebound alkalosis. Therefore, it is perhaps significant in our studies that the pH on the rostral side of the injury was more affected than the caudal side. If impaired neurotransmitter release/uptake is important, and is manifest by increase synaptic leakage of same because of injury, then we might expect the effects to be associated with the part of the cord that contains more synapses. This would be the rostral side because we would expect more synapses exist as one looks closer to the brain.

A main reason it is possible to obtain pH from CSF spectroscopically is that there is little protein to provide spectral congestion and impair clean use of the raw relevant phosphate Raman features in the calculations. The phosphate concentration in normal cord should not exceed 400 µm and the phosphate features are relatively strong from CSF in vivo. These phosphate features occur in or near troughs as well as peaks in the raw baseline corrected Raman spectra. Because of some baseline subtraction procedures in biomedical Raman spectroscopy, it is assumed that there is no Raman activity in regions that resemble a trough in the baseline corrected Raman spectra. However, some of these approaches would fail to pick up the changes that led to this successful measurement of pH. The 101-7 procedure always avoids this pitfall but other approaches may fail or succeed.

The ability to measure pH immediately suggests that such measurements could be done in a manner to allow creation of a dynamic pH image or map of e.g. an injured spinal cord. Our earlier work employed the PV[O]H algorithm to create images based on the underlying distribution of fluids and turbidity and it would be natural to include pH into such images. Future work could endeavor to increase the size of the cohorts with respect to the CSI study. Perhaps most intriguing is the unambiguous observation that these experiments used, e.g., 10 mM PBS and most of the species were at concentrations in the $10^2$ mM range.

The pH of CSF has thus been measured noninvasively and in vivo in rat and swine model spinal cords, and the present invention has been validated in the swine model by direct comparison with analysis of simultaneously physically sampled CSF. There is a significant difference between pH of CSF in injured rat cord compared to Controls. The pH of CSF in injured cord is higher than in Controls and tends to be higher rostral to the injury and the CSF caudal is not affected or is affected less.

What is claimed is:

1. A system for determining pH, comprising:
   a Raman spectrometer configured to collect Raman spectra from a target of cerebral spinal fluid in vivo using a predetermined excitation wavelength over a predetermined exposure time;
   a microprocessor coupled to the Raman spectrometer that is programmed to exclude any elastically scattered light, crop any collected Raman spectra to a predetermined range of Raman shift to provide a list of counts for a corresponding list of wavenumbers in the predetermined range, to smooth the list of counts using equal weights to produce a smoothed function, to baseline subtract the smoothed function from the collected Raman spectra to provide a baseline subtracted spectra, and to calculate a pH for the cerebral spinal fluid based on the baseline subtracted Raman spectra.

2. The system of claim 1, wherein the predetermined excitation wavelength is 785 nanometers.

3. The system of claim 2, wherein the predetermined exposure time is five minutes.

4. The system of claim 1, wherein the microprocessor is programmed to baseline subtract the collected Raman spectra using a 101-7 procedure.

5. The system of claim 4, wherein the microprocessor is programmed to calculate the pH for the target according to the formula:

$$pH=pK_{a2}+\log([HPO_4^{-2}]/[H_2PO_4^{-1}]).$$

6. The system of claim 5, wherein $[HPO_4^{-2}]$ is determined based on a count of the collected Raman spectra at 1072 $cm^{-1}$.

7. The system of claim 6, wherein $[H_2PO_4^{-1}]$ is determined based on a count of the collected Raman spectra at 985 $cm^{-1}$.

8. A method of measuring a pH, comprising the steps of:
   using a Raman spectrometer to collect Raman spectra from a target of cerebral spinal fluid in vivo at a predetermined excitation wavelength over a predetermined exposure time;
   receiving the collected Raman spectra;
   baseline subtracting the collected Raman spectra by excluding any elastically scattered light, cropping any collected Raman spectra to a predetermined range of Raman shift to provide a list of counts for a corresponding list of wavenumbers in the predetermined range, smoothing the list of counts using equal weights to produce a smoothed function, and baseline subtracting the smoothed function from the collected Raman spectra to provide a baseline subtracted Raman spectra; and
   calculating a pH for the cerebral spinal fluid based on the baseline subtracted Raman spectra.

9. The method of claim 8, wherein the predetermined excitation wavelength is 785 nanometers.

10. The method of claim 9, wherein the predetermined exposure time is five minutes.

11. The method of claim 10, wherein the step of baseline subtracting the collected Raman spectra uses a 101-7 procedure.

12. The method of claim 11, wherein the step of calculating the pH for the target uses the formula:

$$pH=pK_{a2}+\log([HPO_4^{-2}]/[H_2PO_4^{-1}]).$$

13. The method of claim 12, wherein $[HPO_4^{-2}]$ is determined based on a count of the collected Raman spectra at 1072 $cm^{-1}$.

14. The method of claim 13, wherein $[H_2PO_4^{-1}]$ is determined based on a count of the collected Raman spectra at 985 $cm^{-1}$.

* * * * *